United States Patent [19]

Potter et al.

[11] 4,438,177

[45] Mar. 20, 1984

[54] CURED PRESSURE SENSITIVE ADHESIVES

[75] Inventors: William D. Potter, Bishop's Stortford Herts; Sinan B. Kiamil, Harlow, both of United Kingdom

[73] Assignee: Smith and Nephew Associated Companies Ltd., London, England

[21] Appl. No.: 389,009

[22] Filed: Jun. 16, 1982

[30] Foreign Application Priority Data

Jun. 17, 1981 [GB] United Kingdom ............... 81-18666

[51] Int. Cl.$^3$ ............................................... B05D 3/06
[52] U.S. Cl. ..................................... 428/355; 427/44; 427/208.4
[58] Field of Search .................... 427/44, 54.1, 208.4; 428/343, 355

[56] References Cited

U.S. PATENT DOCUMENTS 3,661,618 5/1972 Brookman et al. ................... 427/44
3,729,338 4/1973 Lehmann et al. ................ 427/208.4
4,234,662 11/1980 Pastor et al. .......................... 427/44

Primary Examiner—John H. Newsome

[57] ABSTRACT

A process for the preparation of an adhesive layer on a substrate which comprises applying to a substrate a composition of an acrylate rendered curable by the presence of a cross linking agent and curing it by electron beam radiation characterized in that the curable composition comprises a liquid alkyl acrylate polymer having a K value of less than 30 in particular a process for preparing cured pressure sensitive adhesive layers for surgical products and products of the process are described.

16 Claims, No Drawings

CURED PRESSURE SENSITIVE ADHESIVES

The present invention is concerned with a process for preparing cured acrylic pressure sensitive adhesive layers by applying an acrylate composition containing a cross-linking agent to a substrate and curing it by electron beam radiation and in particular a process of preparing cured pressure sensitive adhesive layers for surgical products and products of the process.

It is well known in the art that the cohesive properties of pressure sensitive adhesives can be improved by curing. Usually this is achieved by heating a pressure sensitive composition which contains a heat reactive cross-linking resin.

U.S. Pat. No. 2,956,906 discloses a method of curing conventional acrylic pressure sensitive adhesives on a substrate by high energy electron irradiation to at least double the cohesive properties of the adhesive. The specification discloses that the adhesives are normally applied to the backing as a solution in an organic solvent. The use of solvents for the manufacture of pressure sensitive adhesives is undesirable for economic and safety reasons. In addition conventional pressure sensitive adhesives which have been post cured are usually too hard for surgical adhesive dressings. The specification also discloses that low molecular weight acrylic polymers can be cured by elecron irradiation to form cured pressure sensitive adhesive layers but does not disclose the use of a cross-linking agent. A cross-linking agent is necessary to reduce the irradiation energy required to cure the polymer.

British Patent Specification No. 1,298,019 discloses a process for preparing a pressure sensitive product which comprises applying to a backing material a monomeric layer of a liquid alkyl acrylate composition, optionally containing a polyfunctional acrylic monomer, having an adjusted viscosity of 100 centipoises and subjecting the layer to high energy particle radiation. However, a large amount of radiation energy is required to convert the liquid alkyl acrylate monomer layer into a cohesive cured pressure sensitive adhesive. In addition the adhesive may still contain residual monomer which is highly undesirable in adhesives required for surgical products. The use of monomers in the process can also cause toxic and safety hazards.

U.S. Pat. No. 3,897,295 discloses a method of forming a pressure sensitive adhesive by applying to a release paper a solventless syrup of an acrylic monomer or monomers and a homopolymer or copolymer of the same monomers optionally containing a polyfunctional acrylate and subjecting the coating to a high energy ionising radiation. The inclusion of a polymer into the monomer coating layer may reduce the radiation energy required to cure the layer but does not eliminate the safety and toxicity hazards of the monomers.

British Patent Specification No. 1,310,328 discloses a method of forming pressure sensitive adhesives by heating a solventless acrylic composition of one or more tacky low molecular weight polymers to a temperature sufficiently above the melting point to maintain it as a hot melt, applying the hot melt to a backing and subjecting the composition to ionising irradiation, the composition before irradiation having a Williams Plasticity of up to 1.5. A polyfunctional acrylic monomer can be present in the composition.

British Application No. 2048274A discloses a method of forming a pressure sensitive adhesive layer on a substrate by applying a layer of molten pressure sensitive adhesive material to the substrate comprising a copolymer of a major amount of one or more pressure sensitive adhesive forming acrylic monomers and a minor amount of allyl acrylate or allyl methacrylate and curing the copolymer in situ by electron beam radiation.

The methods disclosed in BP No. 1,310,328 and G.B. 2048274A avoid the use of solvents or liquid monomers by using a prepolymer for the pressure sensitive adhesive forming layer which is applied to the substrate as a hot melt. However both these patents disclose that the prepolymers need to be heated to a temperature of 120° C. to 180° C. to obtain a suitable low viscosity for coating. The use of hot melt prepolymers has the disadvantage of requiring special hot melt coating equipment which is more expensive to operate than conventional coating equipment and the elevated coating temperatures required limits the number of substrates to which the prepolymers can be directly applied.

A simple and economic process has now been discovered for preparing cured acrylic pressure sensitive adhesive layers by electron beam radiation which process reduces or eliminates the need to use solvents, liquid monomers or heat to apply the layer to the substrate.

The present invention provides a process for the preparation of an adhesive layer on a substrate which comprises applying to the substrate a composition of an acrylate rendered curable by the presence of a cross-linking agent and curing it by electron beam radiation characterized in that the curable composition comprises a liquid alkyl acrylate polymer having a K value of less than 30.

A liquid alkyl acrylate polymer means an alkyl acrylate polymer which does not undergo a phase change when heated. Suitable alkyl acrylate polymers are liquid at ambient room or slightly elevated temperatures for example at temperatures of 20° C. to 60° C. and more suitably 10° to 70° C. The preferred liquid alkyl acrylate polymers have a K value of not less than 10. K values are determined according to H. Fikentscher, Cellulose Chemie 13 58, (1932).

To enable the liquid polymers to be applied to a substrate by conventional coating equipment, the polymers should have a viscosity of less than 1500 poise and preferably a viscosity of 1000 poise at 20 sec$^{-1}$ shear rate at 10° C. to 60° C.

The liquid polymer will be a polymer of one or more alkyl acrylate monomers normally present in acrylic pressure sensitive adhesives. Suitable monomers are alkyl esters of acrylic acid in which the alkyl groups have 4 to 12 carbon atoms and preferably have 4 to 8 carbon atoms. Preferred alkyl acrylates are n-butyl acrylate, 2-ethyl hexyl acrylate and iso-octyl acrylate.

The alkyl acrylate component of the polymer can be from 84% to 98% and preferably can be from 87% to 95% by weight of the polymer. Other monofunctional monomer units may be present in the polymer. Preferred monomer unit is acrylic acid. Acrylic acid component of the polymer can be present in amounts up to 10% by weight of the polymer, desirably in amounts of 4% to 8% and preferably in amounts of 5% to 7% by weight of the polymer.

One or more crosslinking agent may be present in the curable composition. Preferred crosslinking agents are polyfunctional acrylates or methacrylates. In a preferred aspect of the invention the crosslinking agent is part of the liquid polymer. Preferred liquid polymers consist of a major amount of one or more alkyl acrylates and a minor amount of a copolymerisable polyfunctional acrylate or methacrylate.

Suitable copolymerisable polyfunctional acrylates or methacrylates have functional groups with different reactivities. Desirably the faster reacting functional groups will take part in the polymerisation reaction leaving the slower reacting functional groups as unreacted pendant groups which can be available to crosslink the polymer on irradiation. However it is important to avoid extensive crosslinking in the liquid prepolymer as this would lead to undesirable gel formation. Suitable copolymerisable crosslinking agents include difunctional acrylates or methacrylates of allyl, vinyl and 1,2-disubstituted unsaturated compounds. Preferred crosslinking agents are allyl acrylate and allyl methacrylate. In the absence of other crosslinking agents the difunctional copolymerisable acrylate or methacrylate can be present in the liquid polymer in amounts up to 6% by weight of the polymer, desirably in amounts of 2% to 4% and preferably in amounts of 2.5% to 3.5% by weight of the polymer.

In another aspect of the invention the curable composition can consist of a liquid polymer and a polyfunctional acrylate or methacrylate crosslinking agent. Preferred polyfunctional acrylate or methacrylate crosslinking agents have functional groups of equal reactivity.

Suitable polyfunctional acrylate or methacrylate crosslinking agents for the liquid polymer include the diacrylate or dimethacrylate esters of ethane diol, butane diol, hexane diol, polyethylene glycol and propylene glycol, trimethylol propane triacrylate and trimethacrylate and pentaethythritol tetra-acrylate and tetramethacrylate.

In the absence of a copolymerisable crosslinking agent in the liquid polymer, the added polyfunctional acrylate or methacrylate crosslinking agent can be present in amounts up to 10% and preferably in amounts of 5% to 10% by weight of the polymer. When both crosslinking agents are used in the liquid curable composition then it is preferred that the copolymerisable polyfunctional acrylate or methacrylate should be present in amounts of up to 4% by weight of the polymer and the added polyfunctional acrylate or methacrylate should be present in amounts of up to 5% by weight of the polymer.

Suitable liquid curable compositions can comprise a liquid copolymer of butyl acrylate, 2-ethylhexyl acrylate, acrylic acid and allyl methacrylate or mixtures thereof with a polyfunctional acrylate or methacrylate.

A preferred liquid curable composition is a liquid polymer of butyl acrylate (45%), 2-ethylhexyl acrylate (45%), acrylic acid (6%) and allyl methacrylate (4%). Other preferred liquid curable compositions consist of a liquid polymer of butyl acrylate (46%), 2-ethylhexyl acrylate (46%), acrylic acid (6%) and allyl methacrylate (2%) mixed with butane diol di-acrylate (5%) or hexane diol di-acrylate (5%).

The liquid polymers can be prepared by polymerising the monomers in a heated reaction vessel with a stirrer under reflux in the presence of a solvent with a high chain transfer coefficient and a catalyst with a short half life. Suitable solvents include isopropyl alcohol, industrial methylated spirit, chlorinated hydrocarbons and the like. Suitable catalysts are peroxides such as peroxydicarbonates. A preferred catalyst is dicyclohexyl peroxydicarbonate. The catalyst is preferably added as a solution gradually to the reaction mixture in aliquot parts during a period of polymerisation reaction. This procedure ensures the resultant polymer has a low molecular weight that is a K value of 10 to 30. In an alternative procedure a mixture of the catalyst and monomers can be added gradually in aliquot parts to the refluxing solvent reaction mixture.

A polymerisation inhibitor can be added to the liquid polymer to prevent further polymerisation taking place during the processing of the liquid polymer, for example during a purification process, which may involve a heating step. Suitable polymerisation inhibitors include butylatedhydroxytoluene, methoxyhydroquinone, phenothiazine and spiroindene. Preferably the polymerisation inhibitor is also an antioxidant. A favoured combined polymerisation inhibitor and antioxidant is a phenolic derivative known as Permanax WSL available from Vulnax Limited. The polymerisation inhibitor can be present in the liquid polymer in amounts of up to 2% and preferably in amounts up to 1% by weight of the polymer. The solvent can be stripped from the liquid polymer using a suitable film evaporator for example a rotary film evaporator or a white wall evaporator. Optionally steam stripping may be used to remove residual monomer from the liquid polymer to produce an odourless product.

The polyfunctional acrylate or methacrylate if required can be added to the liquid polymer by simply mixing the two materials by stirring in a suitable container.

To prepare a cured pressure sensitive layer the liquid curable composition is applied to a substrate and cured by electron beam radiation.

The liquid curable composition can be applied to a substrate by a conventional coating process including doctor blade over flat bed, doctor blade over roller and reverse roller techniques.

Depending on the rheological properties of the liquid polymer composition it may be convenient to heat the composition to a temperature of up to 70° C. before or during its application to the substrate.

The substrate can be a release surface such as silicone coated paper or film or the like from which the adhesive can be transferred to another substrate such as a woven, knitted or non woven fabric. Alternatively the substrate can be a continuous, microporous or macroporous film or sheet which is suitable as a backing for adhesive tape or surgical adhesive dressing. Suitable backings include films of plasticised polyvinyl chloride, microporous polyvinyl chloride, polyurethane, polyethylene terephthalate and unplasticised polyvinyl chloride.

The liquid composition can be cured by passage under electron beam radiation at a dose level of 2.5 to 10 megarads and preferably at a dose level of 4 to 6 megarads.

A convenient source of electron beam radiation is an 'Elecron Curtain' equipment made by Energy Science Inc. Typical curing conditions using this equipment are voltage 150 Kv beam current 2.5 milli-amps at processing speed of 50 feet/minute to give a total radiation dose of 5 megarads.

The resultant cured pressure sensitive adhesive can be used on surgical dressings. The adhesives have good adhesion to skin and do not fail cohesively when removed from the wound site.

For surgical dressings the coating weight of a cured acrylic pressure sensitive adhesive made by the method of the invention can be 10 to 250 g/m$^2$, desirably 20 to 100 g/m$^2$ and preferably 30 to 50 g/m$^2$. The cured pressure sensitive adhesives may also be used for industrial tapes.

In a further aspect the present invention provides surgical dressings and industrial adhesive tapes carrying a cured acrylic pressure sensitive adhesive made by the process of the invention.

Preparation of Liquid Curable Compositions (a) n-butylacrylate (188 g), 2-ethylhexyl acrylate (188 g), acrylic acid (24 g) and allyl methacrylate (16 g) monomers together with isopropanol (360 g) were added to a reactor vessel and heated under reflux until the mixture reached a temperature of 80° C. A solution of dicyclohexyl peroxydicarbonate catalyst (0.28 g) in isopropyl alcohol (40 g) was added in five aliquots over a period of 50 minutes. The reaction mixture was heated under reflux with stirring for a further period of 2 hours. The reaction mixture was then stripped of solvent by a rotary evaporator. The resultant liquid polymer had a K value of 21 and a viscosity of 4300 poise at 25° C. and 20 sec$^{-1}$ shear rate.

(b) A liquid polymer was made in the same manner as that in (a) described above except that 8 g of allyl methacrylate monomer was used instead of 16 g. The resultant liquid polymer had a K value of 27 and a viscosity of 5000 poise at 25° C. at a 20 sec$^{-1}$ shear rate. Hexane diol diacrylate (20 g) was mixed into the liquid composition.

(c) n-butyl acrylate (23.5), 2-ethylhexyl acrylate 23.5 g) acrylic acid (3 g) and allyl methacrylate (2 g) were pre-mixed and added over a 20 minute period together with a solution of dicyclohexyl peroxydicarbonate (0.023 g) in isopropyl alcohol to a reaction vessel containing isopropyl alcohol (200 g) refluxing at 80° C. After addition of all the monomers a further 0.047 g of dicyclohexyl peroxydicarbonate dissolved in isopropyl alcohol was added over 70 minutes to the refluxing reaction mixture. Reflux was continued for a further 30 minutes bringing the total reaction time to 2 hours. A phenolic antioxidant (0.6% by weight of polymer of Permanax WSL) was added and the product stripped on a rotary evaporator to remove solvent and unreacted monomer. The resultant liquid polymer had a K value of 14 and a viscosity of a 1,200 poise at 25° C. and 200 sec$^{-1}$ shear rate.

EXAMPLE 1

The liquid curable composition (a) as prepared above was heated to 40° C. and coated onto a silicone release coated paper (Steralease 15 from Sterling Coated Papers Ltd.) by a doctor blade over flat bed coating unit to give a mass weight of 40 g/m$^2$. The coated composition was then cured by exposure to 5 megarads of electron beam radiation (Electric Curtain equipment made by Energy Science Inc.) to give a crosslinked pressure sensitive adhesive.

EXAMPLE 2

The curable liquid composition (b) was coated onto a silicone coated release paper and cured by exposure to electron beam radiation in the same manner as Example 1 to form a crosslinked pressure sensitive adhesive.

EXAMPLE 3

The curable liquid composition (c) was coated onto a silicone coated release paper and cured by exposure to electron beam radiation in the same manner as example 1 to form a crosslinked pressure sensitive adhesive.

What is claimed is:

1. Process for the preparation of an adhesive layer on a substrate which comprises applying to a substrate a composition of an acrylate rendered curable by the presence of a crosslinking agent and curing it by electron beam radiation characterised in that the curable composition consists essentially of a liquid alkyl acrylate polymer having a K value of 10 to 30 and a polyfunctional acrylate or methacrylate crosslinking agent said liquid alkyl acrylate polymer containing copolymerisable polyfunctional acrylate or methacrylate monomer units to provide an additional crosslinking agent.

2. A process as claimed in claim 1 in which the liquid alkyl acrylate polymer contains one or more alkyl esters of acrylic acid in which the alkyl groups have 4 to 12 carbon atoms.

3. A process as claimed in claim 1 in which the liquid alkyl acrylate polymer contains acrylic acid monomer units.

4. A process as claimed in claim 1 in which the liquid acrylate polymer contains 4% to 8% by weight of the polymer of acrylic acid monomer units.

5. A process as claimed in claim 1 in which the liquid alkyl acrylate polymer contains up to 6% by weight of the polymer of copolymerisable polyfunctional acrylate or methacrylate monomer units.

6. A process as claimed in claim 5 in which the liquid alkyl acrylate polymer contains 2% to 6% by weight of the polymer of copolymerisable polyfunctional acrylate or methacrylate monomer units.

7. A process as claimed in claim 5 in which the copolymerisable polyfunctional acrylate or methacrylate is allyl acrylate or allyl methacrylate.

8. A process as claimed in claim 1 in which the curable composition contains up to 10% by weight of the polymer of a polyfunctional acrylate or methacrylate crosslinking agent.

9. A process as claimed in claim 8 in which the curable composition contains 5% to 10% by weight of the polymer of a polyfunctional acrylate or methacrylate cross linking agent.

10. A process as claimed in claim 1 in which the liquid alkyl acrylate polymer is a copolymer of butyl acrylate 2-ethylhexyl acrylate, acrylic and allyl methacrylate.

11. A process as claimed in claim 1 in which the liquid alkyl acrylate polymer is prepared by polymerising the monomers in the presence of a solvent with a high chain transfer coefficient.

12. A process as claimed in claim 1 in which the curable composition is cured by passage under electron beam radiation at a dose level of 4 to 6 megarads.

13. A process as claimed in claim 1 in which the adhesive is a pressure sensitive adhesive.

14. An industrial tape carrying a cured acrylate pressure sensitive adhesive made by the process of claim 1.

15. A surgical dressing carrying a cured acrylic pressure sensitive adhesive made by the process of any claim 1.

16. A surgical dressing as claimed in claim 15 in which the weight per unit area of the cured acrylic pressure sensitive adhesive layer is 20 to 100 g/m$^2$.

* * * * *